United States Patent
Callister

(10) Patent No.: US 10,338,016 B1
(45) Date of Patent: Jul. 2, 2019

(54) VERIFICATION OF MATERIAL COMPOSITION IN PRECIOUS METAL OBJECT

(71) Applicant: Jeffrey Callister, Deephaven, MN (US)

(72) Inventor: Jeffrey Callister, Deephaven, MN (US)

(73) Assignee: Jeffrey Callister, Deephaven, MN (US)

( * ) Notice: Subject to any disclaimer, the term of this patent is extended or adjusted under 35 U.S.C. 154(b) by 252 days.

(21) Appl. No.: 15/279,104

(22) Filed: Sep. 28, 2016

Related U.S. Application Data

(60) Provisional application No. 62/233,855, filed on Sep. 28, 2015.

(51) Int. Cl.
*G01N 25/20* (2006.01)
*G01N 33/20* (2019.01)

(52) U.S. Cl.
CPC ............. *G01N 25/20* (2013.01); *G01N 33/20* (2013.01)

(58) Field of Classification Search
CPC .......... G01N 25/20; G01N 33/20; G07D 5/00; G01J 5/00; G01J 2005/0081; G01J 2005/0085; G01J 5/061; G01J 2005/123; G01J 2005/202
See application file for complete search history.

(56) References Cited

U.S. PATENT DOCUMENTS

| | | | |
|---|---|---|---|
| 3,592,060 A * | 7/1971 | Laverman | G01N 25/18 374/43 |
| 3,733,887 A * | 5/1973 | Stanley | G01N 25/18 374/44 |
| 3,808,439 A | 4/1974 | Renius | |
| 3,981,175 A | 9/1976 | Hammond, III et al. | |
| 4,381,154 A | 4/1983 | Hammond, III | |
| 4,385,843 A | 5/1983 | Hammond, III et al. | |
| 4,630,938 A * | 12/1986 | Piorkowska-Palczewska | G01N 25/18 374/29 |
| 5,052,819 A * | 10/1991 | Baratta | G01N 25/18 374/12 |

(Continued)

OTHER PUBLICATIONS

Junyan, et al. "Research on thermal wave processing of lock-in thermography based on analyzing image sequences for NDT" *Infrared Physics & Technology* 53 (2010) pp. 348-357.

*Primary Examiner* — Lisa M Caputo
*Assistant Examiner* — Philip L Cotey
(74) *Attorney, Agent, or Firm* — Christensen, Fonder, Dardi & Herbert PLLC

(57) ABSTRACT

A system, method, and computer program product for verifying a purported composition of material in a solid metal object based on heat transfer characteristics. Embodiments include determining, using a group of temperature sensors included in a heat sink, a heat transfer profile for the heat sink when connected to the solid metal object. One or more embodiments include comparing the heat transfer profile for the solid metal object to a baseline heat transfer profile determined based on dimensions of the solid metal object and the purported composition. One or more embodiments include determining, based on the comparing, a difference between the heat transfer profile and the baseline heat transfer profile. And one or more embodiments include indicating that the purported composition is verified in response to determining that the difference between the heat transfer profile and the baseline heat transfer profile is within a threshold.

6 Claims, 11 Drawing Sheets

(56) References Cited

U.S. PATENT DOCUMENTS

| | | | | |
|---|---|---|---|---|
| 5,251,980 | A * | 10/1993 | Hiraoka | G01B 7/06 |
| | | | | 374/44 |
| 6,431,748 | B1 | 8/2002 | Baratta | |
| 6,886,976 | B2 * | 5/2005 | Gaasch | G01R 1/0458 |
| | | | | 324/750.09 |
| 6,921,195 | B2 * | 7/2005 | Pipe | G01K 3/00 |
| | | | | 374/32 |
| 6,923,570 | B2 * | 8/2005 | Shih | G01N 3/18 |
| | | | | 374/30 |
| 7,758,239 | B2 | 7/2010 | Ignatowicz | |
| 8,047,708 | B2 * | 11/2011 | Hallen | G01K 17/00 |
| | | | | 374/141 |
| 8,262,989 | B2 * | 9/2012 | Carlsson | G01K 17/006 |
| | | | | 422/51 |
| 2002/0034211 | A1 * | 3/2002 | Baratta | G01N 25/18 |
| | | | | 374/45 |
| 2005/0002435 | A1 * | 1/2005 | Hashimoto | G01N 25/18 |
| | | | | 374/43 |
| 2005/0058178 | A1 * | 3/2005 | Shih | G01N 3/18 |
| | | | | 374/51 |
| 2011/0188534 | A1 * | 8/2011 | Nishimura | G01N 25/4866 |
| | | | | 374/10 |
| 2015/0070035 | A1 | 3/2015 | Blau | |
| 2015/0127294 | A1 * | 5/2015 | Lubner | A61B 5/01 |
| | | | | 702/136 |

\* cited by examiner

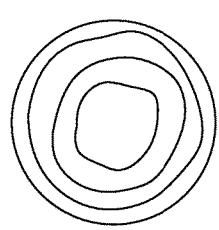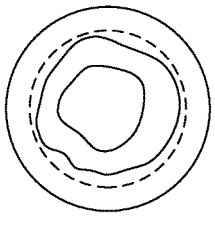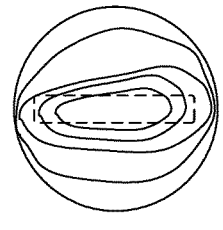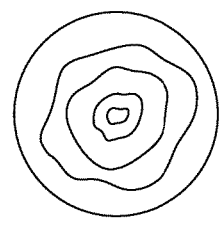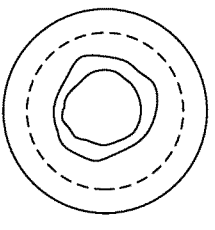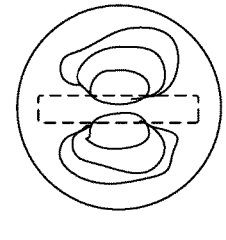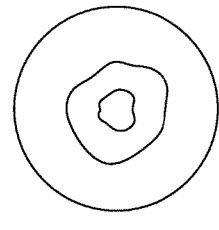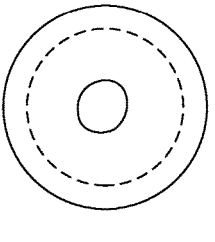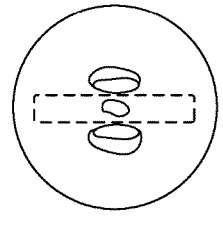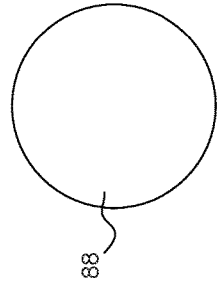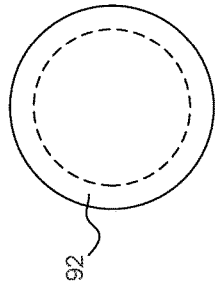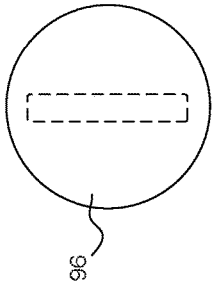
FIG. 8A   FIG. 8B   FIG. 8C

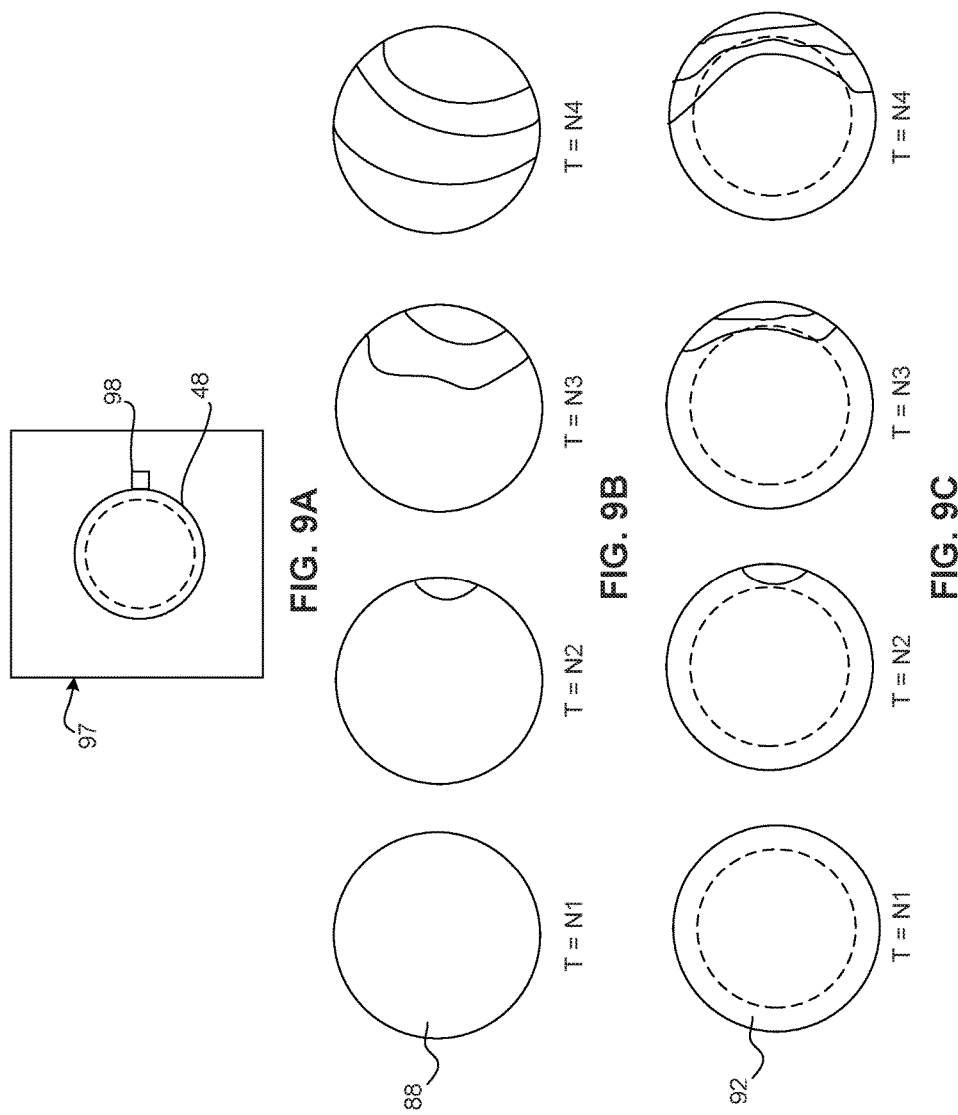

VERIFICATION OF MATERIAL COMPOSITION IN PRECIOUS METAL OBJECT

CROSS-REFERENCE TO RELATED APPLICATION

This application claims the benefit of U.S. Provisional Application No. 62/233,855, filed on Sep. 28, 2015.

BACKGROUND

The present disclosure relates to materials testing, and more specifically, to verifying a purported composition of material in a solid metal object.

Precious metal objects, such as precious coins, bullion bars, or other precious metal objects may be certified or labeled as having a particular composition of material. For example, a gold coin or bar may be certified as having a particular karat rating, indicating that the object is composed of a specific percentage of gold. A coin labeled as "24 karat" is purportedly composed of over 99% pure gold. However, in some instances, while certified as having a particular composition of precious metal, in reality, the coin or bar may actually be composed of an exterior layer of precious metal hiding relatively low cost metal in the interior of the coin or bar.

For example, an unscrupulous person could fabricate a fake 10 oz gold bullion bar that, in reality, includes a 6.0 oz slug of tungsten clad with 4.0 oz of gold. The person could then imprint the design and mint signatures from a reputable gold supplier on the bar to mislead consumers as to the actual value of the item. At today's price of gold at around $1200 per ounce verses the price of tungsten at around $30 per kilogram, a consumer would be cheated out of $7200.00 of gold.

This interior metal slug may be difficult to detect by visual, dimensional/weight or surface testing. For example, tungsten and gold have a have a similar density (e.g. Tungsten has a density of approximately 19.35 g/cm$^3$ while Gold has a density of approximately 19.32 g/cm$^3$, a difference of approximately 0.16%). Thus, a supposedly gold coin or bar that includes a slug of tungsten will be nearly identical to a coin or bar made entirely of gold. Additionally, with computer aided manufacturing technology, it has become cheaper and easier to produce these type of fake coins and bars.

Known methods for verifying the purity of a coin or bar have consisted of visual verification by inspection of a drilled or cut sample of material from the object. Additional known methods for verifying consisted of melting point comparison by melting a sample of the material, and X-ray or ultrasound analysis. However, these methods are undesirable as they may result in damage to the original coin or bar, devalue the object, require specialized equipment, are cost prohibitive, and are time consuming. Accordingly, an improved method of verifying the purity of a coin or bar is desirable.

SUMMARY

Aspects of the disclosure are directed to methods and systems for verifying a purported composition of material in a solid metal object. One or more embodiments utilize the differences in the thermal conductivity of different metals for verifying a purported composition of precious metal in a metal object, such as a coin, bullion bar, or other precious metal object. All metals have a rate at which heat/energy is transferred through the metal. This property is denoted as thermal conductivity. The higher the thermal conductivity of a metal, the more readily heat is conducted through the metal. For example, silver (Ag) has the highest thermal conductivity of any metal at approximately 429 (W/(m×K)), gold has a thermal conductivity of approximately 318 (W/(m×K)), and tungsten is approximately 173 (W/(m×K)). When metals are in contact, heat transfer between the metals is rate dependent on the metal having the lowest thermal conductivity, e.g. be heat cannot transfer faster than the rate indicated by the smallest thermal conductivity.

Another property that affects heat transfer in a transient mode is the thermal capacitance of the material. A certain amount of energy must be transferred to a material before the material will undergo an attendant rise in temperature. A parameter that characterizes the thermal capacitance of a material is referred to as the specific heat of the material, with units, for example, of Joules per kilogram per degree Kelvin (J/kg·K). The specific heat influences the thermal profile of an object as it is being heated up; that is, the specific heat affects the "transient" thermal profile. Another property that characterizes the transient response of a material is the diffusivity ($\alpha$), taken as the ratio of the conductivity (k) to the product of the density ($\rho$) and the specific heat (Cp):

$$\alpha = k/\rho \cdot Cp$$

Units of diffusivity are, for example, meters squared per second (m$^2$/s). The diffusivity of gold is 127×10$^{-6}$ m$^2$/s, while that of tungsten is 68×10$^{-6}$ m$^2$/s—about half that of gold. Accordingly, transient temperature profiles will vary substantially between gold and tungsten.

Accordingly, one or more embodiments of the disclosure determine a heat transfer profile for a metal object based on temperature measurements of a thermally connected heat sink. The heat sink has a temperature differential with the metal object and temperature measurements depicts the change in the temperature of the heat sink as heat energy transfers between the two. Embodiments of the disclosure compare the heat transfer profile with a baseline profile, based on the purported composition of material and the dimensions of the metal object, and determine whether the composition of material is verified. Both steady state and transient thermal profiles are contemplated.

Embodiments of the disclosure provide benefits in precious metal testing accuracy, reliability, and reduced risk of damage to a precious metal object. For example, embodiments of the disclosure verify the composition of material in a solid metal based on heat transfer characteristics of the solid metal object without requiring drilling, cutting, or otherwise modifying the solid object. Additionally, embodiments provide a process that is relatively simple to perform and does not require specialized imaging equipment.

One or more embodiments includes a test bed including a heat sink for connection to a metal object having purported composition of material. The heat sink includes a group of one or more temperature sensors that are communicatively connected to a controller for measuring the temperature of the heat sink. In certain embodiments, the controller is configured to determine a heat transfer profile for the metal object by sensing temperature of the heat sink over a testing interval when thermally connected to the metal object. In one or more embodiments, the heat transfer profile is compared to a baseline profile based on the purported composition of material and the physical dimensions of the metal object. In one or more embodiments the controller determines a difference between the baseline profile and the heat transfer profile and, based on the difference, indicates whether the purported composition of material is verified.

One or more embodiments of the disclosure are directed to a system for verifying a purported composition of material in a solid metal object based on heat transfer characteristics. In certain embodiments, the system includes a heat sink including a group of temperature sensors therein and a controller communicatively connected to the group of temperature sensors. In various embodiments, the controller includes a processor and a memory, the memory including a set of instructions. In one or more embodiments, the set of instructions are executable on the processor to determine, using the group of temperature sensors, a heat transfer profile for the heat sink when connected to the solid metal object, the heat transfer profile indicating temperature of the heat sink with the solid metal object over a testing interval, the heat sink having a temperature differential with the solid metal object at least at a beginning of the testing interval. In one or more embodiments, the set of instructions are executable on the processor to compare the heat transfer profile for the solid metal object to a baseline heat transfer profile determined based on dimensions of the solid metal object and the purported composition. In one or more embodiments, the set of instructions are executable on the processor to determine, based on the comparing, a difference between the heat transfer profile and the baseline heat transfer profile. In some embodiments, the set of instructions are executable on the processor to indicate, using the controller, that the purported composition is verified, in response to determining that the difference between the heat transfer profile and the baseline heat transfer profile is within a threshold.

One or more embodiments of the disclosure are directed to a system for verifying a purported composition of material in a solid metal object based on heat transfer characteristics. In various embodiments, the system includes a display case including a plastic chassis defining a cavity therein for storing a solid metal object. In one or more embodiments, the display case includes one or more testing contacts within the cavity for thermal connection to the solid metal object. In some embodiments, the system includes a testing apparatus including a housing defining a slot for insertion of the display case. In one or more embodiments, the housing includes a heat sink including a group of temperature sensors, a heating element connected to the heat sink and a controller. In various embodiments, the controller is communicatively connected to the group of temperature sensors and the heating element, and the controller includes a processor and a memory. In one or more embodiments, the set of instructions are executable on the processor to determine, using the group of temperature sensors, a heat transfer profile for the heat sink when connected to the solid metal object, the heat transfer profile indicating temperature of the heat sink with the solid metal object over a testing interval, the heat sink having a temperature differential with the solid metal object at least at a beginning of the testing interval. In one or more embodiments, the set of instructions are executable on the processor to compare the heat transfer profile for the solid metal object to a baseline heat transfer profile determined based on dimensions of the solid metal object and the purported composition. In one or more embodiments, the set of instructions are executable on the processor to determine, based on the comparing, a difference between the heat transfer profile and the baseline heat transfer profile. In some embodiments, the set of instructions are executable on the processor to indicate, using the controller, that the purported composition is verified, in response to determining that the difference between the heat transfer profile and the baseline heat transfer profile is within a threshold.

The above summary is not intended to describe each illustrated embodiment or every implementation of the present disclosure.

BRIEF DESCRIPTION OF THE SEVERAL VIEWS OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

FIGS. 8A-8C depict thermographic images of a coin on a testing apparatus, according to one or more embodiments.

FIG. 9A depicts a top view of a test bed according to one or more embodiments.

FIGS. 9B-9C depict thermographic images of a coin on a testing apparatus, according to one or more embodiments.

Figure 1:
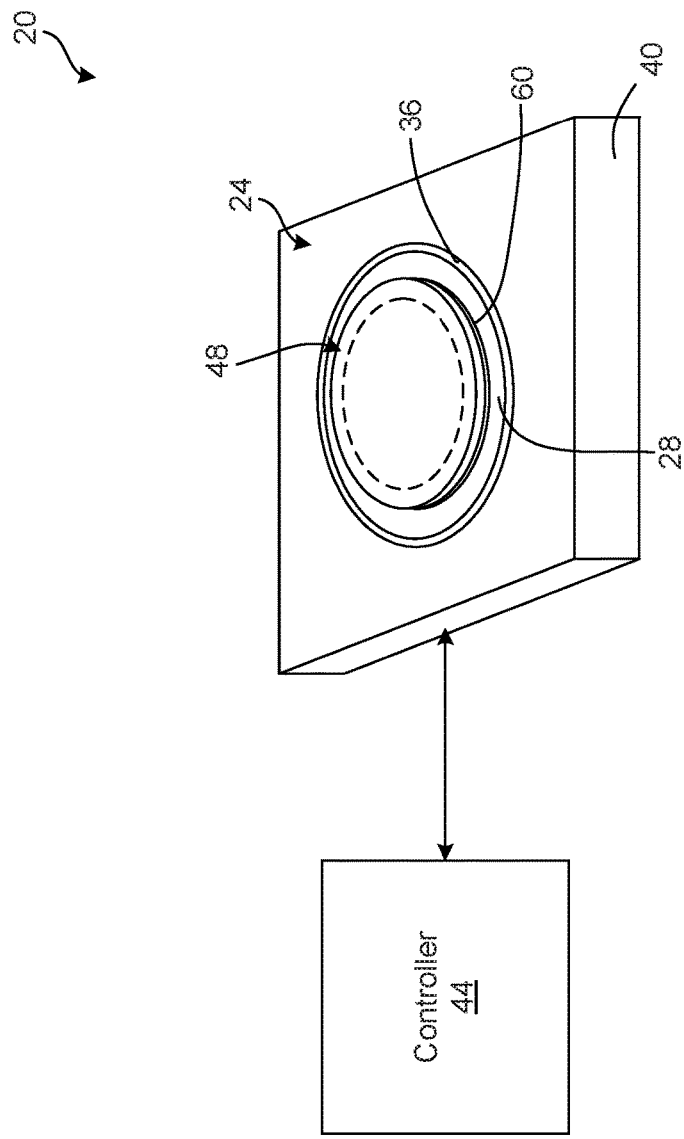
FIG. 1 depicts a perspective view of a testing apparatus, according to one or more embodiments.

While the disclosed embodiments are amenable to various modifications and alternative forms, specifics thereof have been shown by way of example in the drawings and will be described in detail. It should be understood, however, that the intention is not to limit the disclosure to the particular embodiments described. On the contrary, the intention is to cover all modifications, equivalents, and alternatives falling within the spirit and scope of the disclosure.

DETAILED DESCRIPTION

Figure 2:
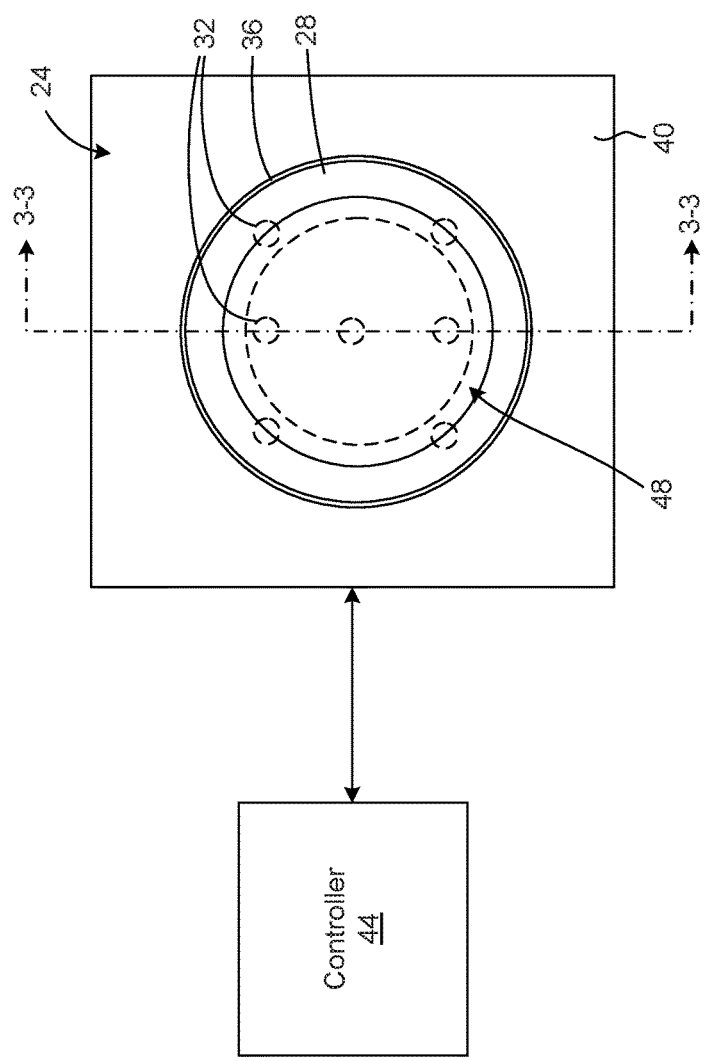
FIG. 2 depicts a top view of a testing apparatus, according to one or more embodiments.
Figure 3:
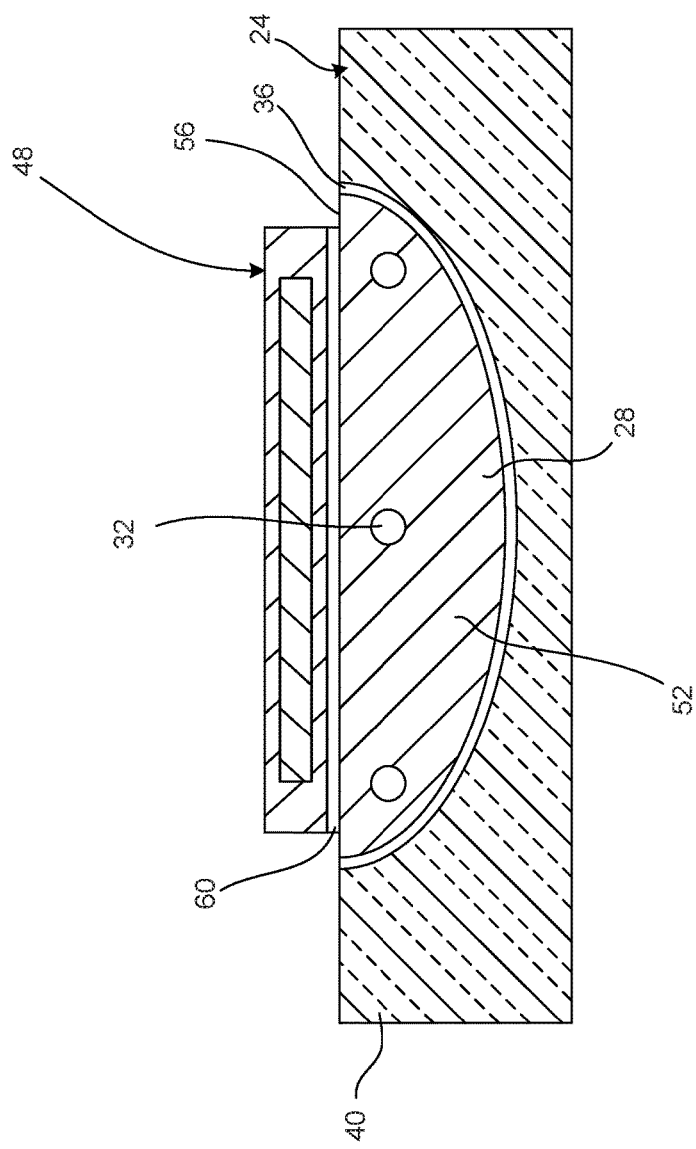
FIG. 3 depicts a cross-section view of a testing apparatus taken at line 3-3 of FIG. 2, according to one or more embodiments.

Referring to FIGS. 1-3, a testing apparatus 20 for verifying a purported composition of material in a solid metal object is depicted, according to one or more embodiments.

The testing apparatus 20 includes a test bed 24 including a heat sink 28, a group of temperature sensors 32, a heating element 36, and an insulated base portion 40. The testing apparatus 20 additionally includes controller 44 communicatively connected to the test bed 24.

In one or more embodiments, the heat sink 28 is a solid metal platform for thermal connection with a metal object 48 for testing by the testing apparatus 20. In one or more embodiments, heat sink 28 includes a body portion 52 defining a flat portion 56 for supporting the metal object 48 on the test bed 24.

In some embodiments, the design of the flat portion 56 corresponds to the shape of the metal object 48. For example, depicted in FIGS. 1-3 the flat portion 56 has a generally circular shape and supports a coin shaped metal object 48. In some embodiments, the flat portion 56 may be used to support a rectangular shaped bar or other shaped object that does not correspond to the shape of the flat portion 56. For example, the heat sink 28 may be formed having a square or rectangular shape having a corresponding rectangular or square shaped flat portion 56 for supporting the metal object 48.

In some embodiments, the heat sink 28 and the flat portion 56 is sized based on the metal object 48 to contact a portion of or all of a surface of the metal object 48. For example, in some embodiments the heat sink 28 is designed to be a point source heat sink, contacting a portion of the metal object 48 such that the flat portion 56 has a surface area at least $\frac{1}{16}^{th}$ as large as a surface of the metal object 48.

In some embodiments, the heat sink 28 is made of silver. Described further herein, because silver is a fast conductor of heat energy, the rate of heat transfer between the metal object 48 and the heat sink 28 will be primarily determined by the composition of material in the metal object 48. Similarly, in some embodiments, the heat sink 28 is made of copper, or other thermally conductive material. The heat sink 28 is partially enclosed in the insulated base portion 40 which thermally isolates the body portion 52 and leaves the flat portion 56 exposed for connection to the metal object 48.

In some embodiments, the flat portion 56 includes a layer of interstitial conductor 60 for connection between the flat portion 56 and the metal object 48. The metal object 48 may include multiple surface features such as surface designs, scrapes, or other features that are not flat. Accordingly, when placed on the flat portion 56, these surface features may create air pockets or portions of the metal object that are recessed and not in contact with the heat sink 28. The conduction of heat energy between two metals at least partially depends on the amount of surface area in contact. Accordingly, interstitial conductor 60, such as a thermal grease or water, may be used to normalize heat transmission between the heat sink 28 and various metal objects 48 which may include different surface features. In embodiments, the interstitial conductor 60 conforms to various surface features in the metal object and compensates for various design features.

In one or more embodiments, the interstitial conductor 60 is a polymerizable liquid matrix with a volume of thermally conductive filler such as, diamond, silver, aluminum nitride, or other suitable thermally conductive filler inert to gold, silver, and/or other precious metals. In some embodiments, the interstitial conductor has a thermal conductivity no less than the thermal conductivity of the metal object 48. Accordingly, heat transfer from the heat sink to the metal object is still controlled by the heat transfer characteristics of the metal object 48. In some embodiments the interstitial conductor is sufficiently solid and pliable such that it leave little to no residue on the metal object and such that the metal object can be impressed in to the interstitial conductor 60.

In some embodiments, the flat surface 56 of the heat sink 28 is a platen that is the reverse/mirror image of a surface of the metal object 48. For example, a coin with specific design features could fit to the heat sink 28 having a mirror image of a portion of design features imprinted into the flat portion 56 to improve the surface contact between the heat sink 28 and the coin. Accordingly, the platen could maximize the surface to surface contact with the metal object 48 without requiring interstitial conductor 60. In some embodiments, the heat sink 28 could include a recessed portion with a sidewall surrounding the recess. The metal object 48 or coin could be inserted into the recess such that the edge of the coin contacts the perimeter of the sidewall. In some embodiments, the heat sink can be two halves in which the coin can be placed in-between them.

In one or more embodiments, the body portion 52 of the heat sink 28 includes a group of one or more temperature sensors 32. Each of the temperature sensors is disposed within the heat sink 28 for sensing the temperature of the heat sink 28. In some embodiments, the group of temperature sensors 32 are electric conduction based thermometers capable of communication with the controller 44. For example, the group of temperature sensors 32 may be thermocouples, resistance thermometers, thermistors, or other suitable temperature sensor.

In one or more embodiments, the heating element 36 is included in the test bed 24 for creating a temperature differential between the heat sink 28 and the metal object 48. In one or more embodiments, the heating element 36 is a resistance based heating device. For example, heating element 36 may be a resistance based heating wire covered in a ceramic material, or other suitable resistance based heating device. However, various other types of heating devices may be used in the testing apparatus 20. For example, in some embodiments, the heating apparatus may be an induction based heating device. In some embodiments heating element 36 may be an fluid based heating/cooling device, such as a gas or a liquid. In some embodiments, the heating element may be an infrared radiation based device. In some embodiments, the heating element 36 is a laser. In certain embodiments, heating element 36 may be cooling element included in the test bed 24 for applying a temperature differential to the heat sink 28.

In one or more embodiments, the controller 44 is a computing device, usable by a consumer or other user, for control of the test bed 24. In some embodiments, the controller 44 may be, for example, a desktop computer, laptop computer, tablet device, smart phone, wearable computing device, or other suitable device. The controller 4 may be include processing elements and memory and may be communicatively connected to the test bed 24 for control of various components in the test bed. For example, controller may be used to measure temperatures from the temperature sensors and/or activate heating element 36 to create the temperature differential in the heat sink. In some embodiments, the controller 44 is a distinct device from the test bed 24 and is connected via a wired and/or wireless connection. In certain embodiments, the controller 44 is included within the test bed 24.

In some embodiments, the controller 44 includes input/output devices for receiving inputs from users and outputting data. The controller may include, for example, a display, a touchscreen, keyboard, mouse, or other input/output device for interfacing with a user via a graphical user interface (GUI) or other user interface.

In operation, the testing apparatus 20 establishes a temperature differential in the heat sink 36 by heating (or in some embodiments cooling) the heat sink 28 using the heating element 36. In some embodiments, the metal object 48 is then thermally connected to the heat sink 28 and the controller 44 initiates a testing sequence. In one or more embodiments, the testing sequence is a series of executable instructions included in memory accessible to the controller and executable by the processor to verify a composition of material in the metal object 48 according to embodiments described herein.

For example, in executing the testing sequence, the controller 44 may initiate a test interval and collect temperature data over the duration of the interval from the temperature sensors 32 in the heat sink 28. As heat transfers from the relatively hot heat sink 28 to the relatively cool metal object 48, the temperature of the heat sink 28 will decrease and approach an equilibrium. In one or more embodiments, based on the collected temperature data, the controller 44 generates a heat transfer profile for the metal object 48.

In one or more embodiments, in executing the testing sequence, the controller 44 determines a baseline profile for comparison with the generated heat transfer profile. The baseline profile may be a heat transfer profile for a different metal object that shares similar dimensions with the tested metal object 48 and has a verified composition of material similar to the purported composition of material.

For example, an American Gold Eagle coin submitted for testing by testing apparatus 20 may be compared with a second American Gold Eagle coin that is known to be authentic. Both coins should share the same or similar dimensions and the same composition of material. Accordingly, the baseline profile based on the authentic coin should substantially match a generated heat transfer profile from the coin submitted for testing. In some embodiments, the baseline profile is generated by prior testing results and is stored in memory accessible to the controller 44. In some embodiments, the baseline profile could be simulated by a computer, or accessed from a database including a library of heat transfer profiles for various different objects.

In one or more embodiments, in executing the testing sequence, the controller 44 determines a difference between the baseline profile and the generated heat transfer profile. In some embodiments, the controller 44 determines the difference by comparing the rate of cooling or heating from the collected data in the heat sink 28, with an expected heating or cooling rate from the base line profile.

For example, if supposedly gold coin has a tungsten slug in it, the rate at which the energy flows out of the coin will be considerably slower vs. a real gold coin. For example, gold has a thermal conductivity of approximately 318 (W/(m×K)), and tungsten has a thermal conductivity of approximately 173 (W/(m×K)). This equates to an approximately 45% difference in the rate of heat transfer. Likewise, tungsten has a thermal diffusivity of approximately $68 \times 10^{-6}$ m²/s, while that of gold is about 100% greater at approximately $127 \times 10^{-6}$ m²/s.

In one or more embodiments, in executing the testing sequence, the controller 44 is configured to verify the purported composition of material in the metal object 48 based on the difference between the generated heat transfer profile and the baseline profile. In embodiments, if the difference between the rate of temperature change exceeds or is outside of an error threshold, then the controller 44 may be configured to indicate, using various input/output devices, that the purported composition of material is not verified. In some embodiments, if the difference does not exceed the threshold or is within the threshold, then the controller 44 may be configured to indicate using input/output devices, that the purported composition of material is verified. In some embodiments, if the difference is no greater than 5%, then the temperature change is within the error threshold.

Additionally, in some embodiments, if the purported composition of material in the metal object is not known, the heat transfer profile could be compared to various baseline profiles to identify the composition of material. For example, if a gold coin has an unknown karat rating, the testing apparatus 20 could be used to compare the heat transfer profile of the coin with various other gold coins having known karat ratings. Because the karat of the coin determines the composition of gold in the coin, the heat transfer profile for each coin should be distinct. In one or more embodiments, if the heat transfer profile substantially matches with one of the baseline profiles, it may be identified as sharing the same composition of material. For example if the unknown coin matches with a baseline profile from a 22 karat coin, the gold coin could be identified as being a 22 karat coin.

Further, in some embodiments, if the starting temperature of both the heat sink and the coin are known, the controller 44 can record the equilibrium temperature of the heat sink and the metal object. The controller 44 may be configured to verify the composition of materials by comparing the results to expected results for an equilibrium temperature based on the heat capacity of the metals.

Figure 4:
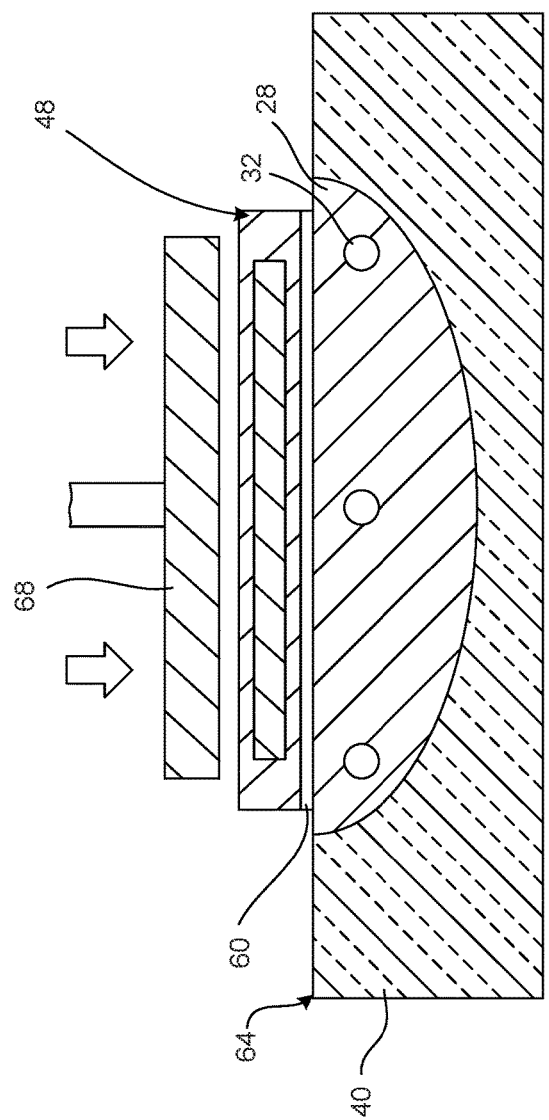
FIG. 4 depicts a cross-section view of a testing apparatus, according to one or more embodiments.

Referring to FIG. 4, a cross-section view of a test bed 64 is depicted according to one or more embodiments of the disclosure. The test bed 64 may be the same or substantially similar as depicted in FIGS. 1-3, and shared elements are indicated by the same reference numerals. For example, test bed 64 includes a heat sink 28 including a group of temperature sensors 32 and surrounded by an insulted base portion 40. A metal object 48 is located on the test bed 64 and connected to the heat sink 48 via interstitial conductor 60.

Depicted in FIG. 4, heating element 68 is located external to the test bed 64 and is placed on the top of the metal object 48 with the coin resting on the heat sink. Similar to FIGS. 1-3, the rate of temperature change in the heat sink 28 is monitored and recorded to determine a heat transfer profile for the metal object 48.

In operation, the heat sink 28 and test bed function in substantially the same manner as test bed 24 in FIGS. 1-3. For example, test bed 64 is communicatively connectable with the controller 44 for execution of testing sequences according to one or more embodiments.

Figure 5:
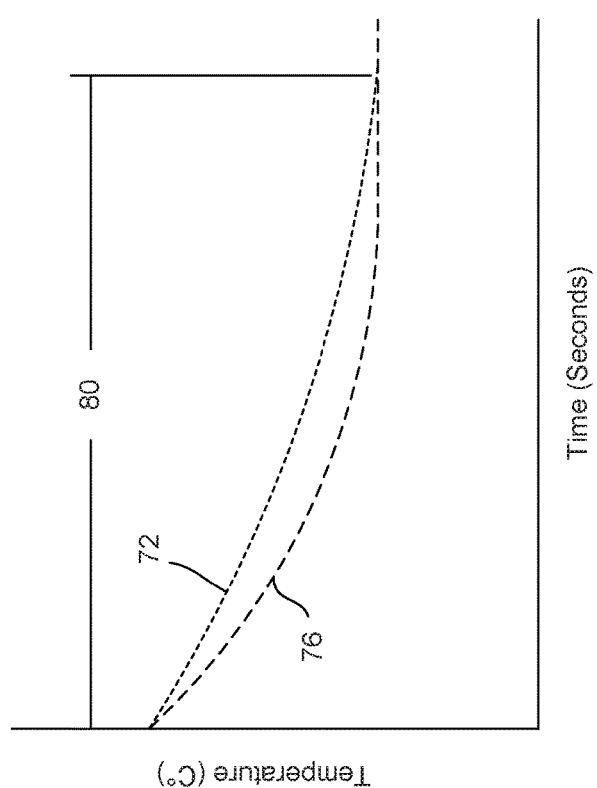
FIG. 5 depicts a temperature plot for a solid metal object and a baseline object on a testing apparatus, according to one or more embodiments.

Referring to FIG. 5 a temperature plot for determining a heat transfer profile is depicted, according to one or more embodiments. As described with reference to at least FIGS. 1-3, each of the temperature plots, 72, 76 depict the temperature change of the heat sink 28 over the course of a testing interval 80. Depicted in FIG. 5, temperature plots 72, 76 are generated using a test bed 24 that, prior to testing, heats the heat sink 28 to create a temperature differential with the metal object. Accordingly, the testing plots 72, 76 show the heat sink cooling, as heat energy transfers from the heat sink 28 into the metal object 48 and the pair reach a thermal equilibrium. In some embodiments, the metal object 48 is heated, as in FIG. 4, or the heat sink 28 is cooled. In those instances, the temperature plots would show the temperature of the heat sink 28 increasing over the course of the testing interval 80.

Plots 72, 76 are depicted for the tested metal object 48 and for a baseline metal object. For example, plot 72 is measured for the metal object 48 having an unverified composition of material. Plot 76 is generated as the baseline profile for comparison with plot 72, as described above. Accordingly, Plot 76 is shows expected heat transfer characteristics for the unverified metal object 48 based on the purported composition of material and the dimensions of the object.

Depicted in FIG. 5, the baseline plot 76 cools more rapidly than plot 72, indicating that heat is transferring between the heat sink 28 and the baseline metal object faster than between the heat sink 28 and the unverified metal object 48. In one or more embodiments, the difference between the plots 72, 76 can be compared by determining a difference in the slope of each of the temperature plots 72, 76 and determining whether that difference exceeds a threshold value to compensate for potential errors in the testing process. If the difference exceeds the threshold, then the testing assembly can determine that the tested coin is not verified.

Figure 6:
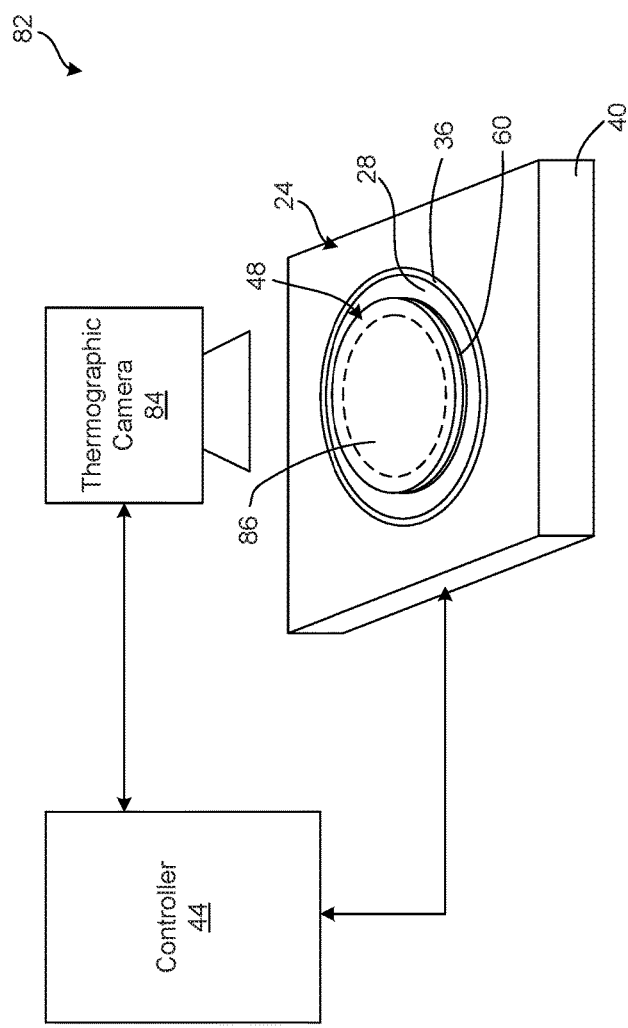
FIG. 6 depicts a perspective view of a testing apparatus including a thermographic camera, according to one or more embodiments.

Referring to FIG. 6 a testing apparatus 82 for verifying a purported composition of material in a solid metal object is depicted, according to one or more embodiments. The testing apparatus 82 may share the same or similar elements of the testing apparatus 20, which are indicated using shared reference numerals. For example, the testing apparatus 82 includes a test bed 24 including a heat sink 28, a group of temperature sensors 32, a heating element 36, and an insulated base portion 40. The testing apparatus 82 additionally includes controller 44 communicatively connected to the test bed 24.

In addition, testing apparatus 82 includes a thermographic camera 84 for infrared imaging of the metal object during the testing interval. As described, the heat sink 28 is either heated or cooled and then placed in contact with the surface of one side of the metal object 84. Alternatively, a heat source could be used in place of the heat sink 28. The other side 86 of the metal object 48 is observed by the thermographic camera 84 and to generate a heat transfer profile further based on observed temperature gradients depicting the change in the temperature of the monitored surface 86 during the testing interval.

Similar to the temperature plots discussed above, the thermographic images depicting the rate of change in temperature of the monitored surface signature will depend on the composition of material in the metal object and the dimensions of the metal object 48. For example, a metal object 48 that includes a slug of low cost material will produce thermographic images noticeably different than an authentic item.

In one or more embodiments, the controller 44 is communicatively connected to the thermographic camera 84 for collection of the thermographic images for generating the heat transfer profile. Additionally, as part of the testing sequence described in reference to FIGS. 1-3, the controller may be configured to compare the collected thermographic images and compare them to a baseline set of images.

Figure 7:
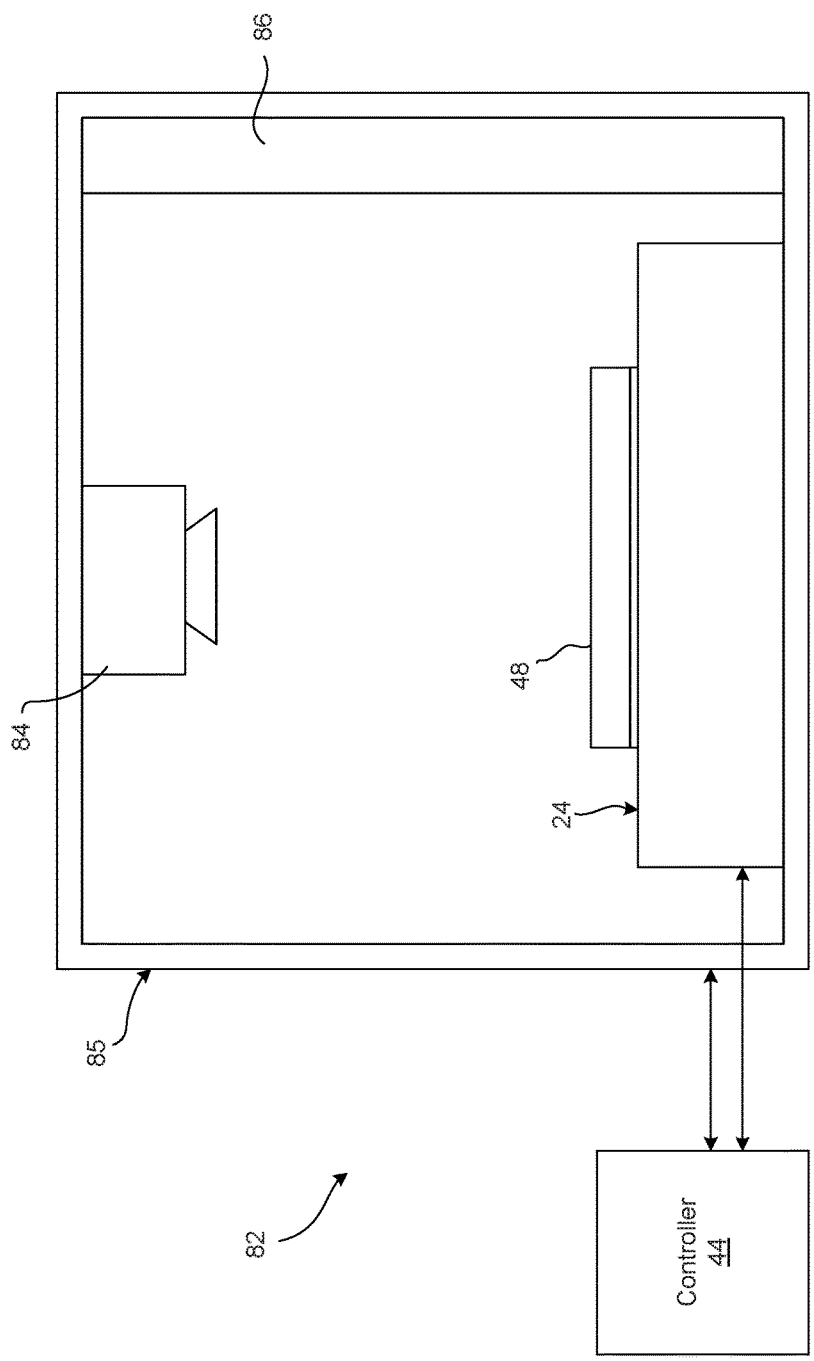
FIG. 7 depicts a side view of a testing apparatus including a thermographic camera in an environmental enclosure, according to one or more embodiments.

Referring to FIG. 7, in one or more embodiments, the testing apparatus 82 may include an environmental enclosure 85 surrounding the test bed 24 and the thermographic camera. In various embodiments, the environmental enclosure includes an environmental control unit 86 that may regulate the temperature, humidity, and/or other various environmental characteristics within the enclosure 85. In one or more embodiments, the enclosure 85 assists in normalizing testing conditions for the metal object 48. For example, in various embodiments, the heat transfer profile may be affected by ambient temperature or other environmental factors. Accordingly, enclosure 85 and environmental control unit 86 may be communicatively connected to the controller 44 to regulate the environment in the enclosure 85 to normalize conditions for the testing apparatus.

Referring to FIGS. 8A-8C, thermographic images of various metal objects, 88, 92, 96 for determining a heat transfer profile are depicted, according to one or more embodiments. FIGS. 8A-8C each depict four thermographic images of a coin tested in testing apparatus 82 over a testing interval of N1 to N4. In some embodiments, the thermographic camera may be configured to take more or fewer images. In some embodiments the thermographic camera is configured to take real time video of the metal objects, 88, 92, 96. Heat, or in some embodiments, cold, is applied to some portion of the bottom side of each coin 88, 92, 96 which then radiates and spreads through the material in the coin. FIGS. 8A-8C each depict different coins 88, 92, 96 having a different composition of material. For example, coin 88 is a solid gold coin, coin 92 has a gold exterior but is filled with a low cost material such as tungsten, and coin 96 has a gold exterior but is filled with a bar of tungsten.

As can be seen in FIGS. 8A-8C, over the course of the testing interval, the thermal gradients for the coins 88, 92, 96 vary. As heat moves through the coins 88, 92, 96 it is rate dependent on the thermal conductivity of material in the coin. Images for coins 92 and 96 differ from coin 88, indicating a difference in thermal conductivity and a difference in the composition of material. In various embodiments, controller 44 may include visual recognition software to analyze and compare thermographic images or video to verify whether the coins match with an authentic coin.

Referring to FIG. 9A a test bed 97 is depicted, according to one or more embodiments. As described, in one or more embodiments the test bed 97 includes a rectangular heat sink 98 that extends upwardly from the test bed 97 and contacts an edge of the metal object 48. Heat is applied to the edge of the metal object 48 which radiates outwardly from the heat sink 98.

Referring to FIGS. 9B and 9C thermographic images of various metal objects 92, 96 are depicted tested in testing apparatus 97 over a testing interval of T=N1 to N4. In some embodiments, the thermographic camera may be configured to take more or fewer images. In some embodiments, the thermographic camera is configured to take real time video of the coins 88, 92, 96. Heat (or in some embodiments, cold) is applied on the side of each coin 88, 92 which then radiates and spreads through the material in the coin. FIGS. 9B-9C each depict different coins 88, 92 having a different composition of material. For example, coin 88 is a solid gold coin, coin 92 has a gold exterior but is filled with a low cost material such as tungsten, and coin 96 has a gold exterior but is filled with a bar of tungsten.

As can be seen in FIGS. 9A-9C, over the course of the testing interval, the thermal gradients for the coins 88, 92 vary. As heat moves through the coins 88, 92 it is rate dependent on the thermal conductivity of material in the coin. Images for coin 92 differs from coin 88, indicating a difference in thermal conductivity and a difference in the composition of material. In various embodiments, controller 44 may include visual recognition software to analyze and compare thermographic images to verify whether the coins match with an authentic coin.

Figure 10:
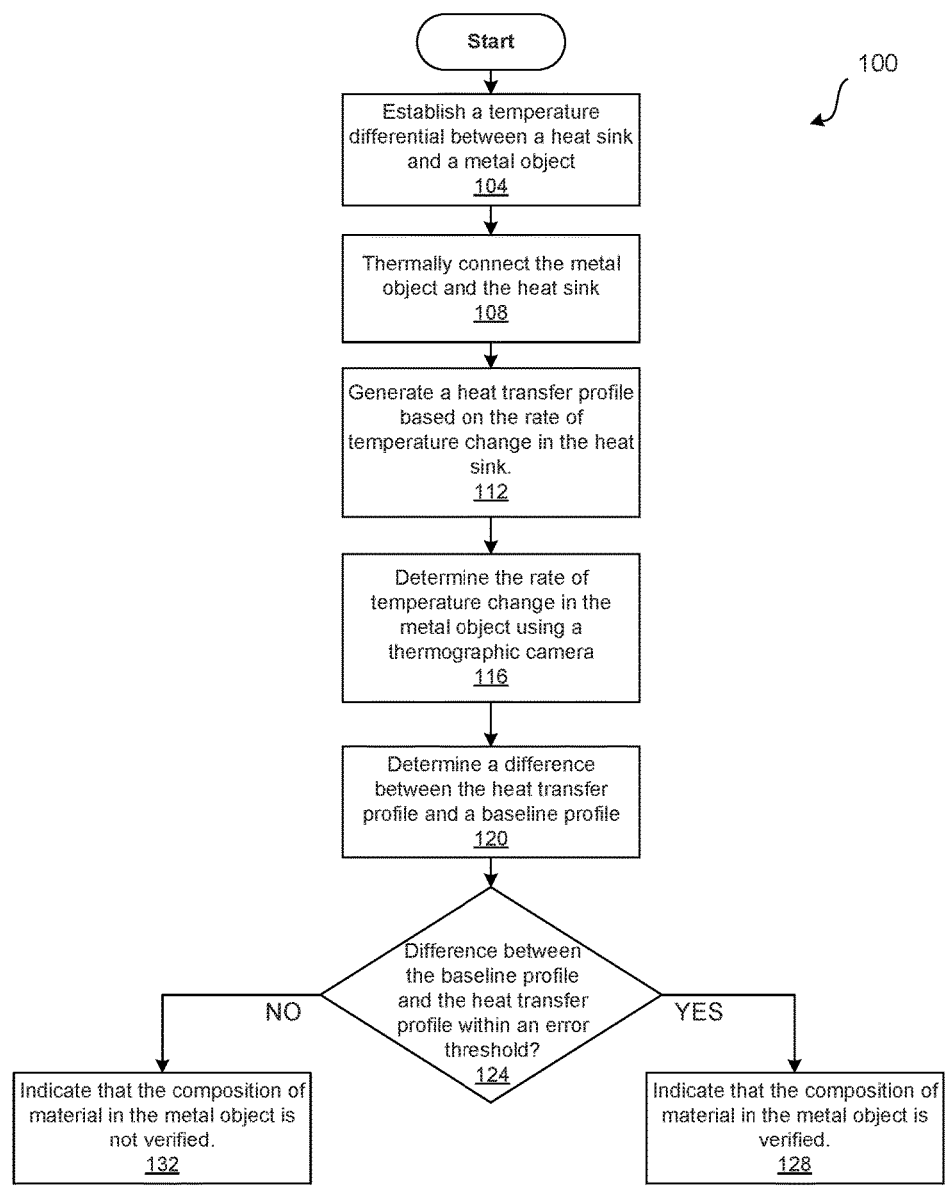
FIG. 10 depicts a flowchart diagram of a method of verifying a purported composition of material in a solid metal object, according to one or more embodiments.

Referring to FIG. 10, a flowchart diagram of a method 100 of verifying a purported composition of material in a solid metal object is depicted, according to one or more embodiments of the disclosure. In operation 104, the method 100 includes establishing a temperature differential between a heat sink and a metal object. In operation 108, the method 100 includes thermally connecting the metal object and the heat sink. In operation 112, the method 100 includes generating the heat transfer profile for the metal object based on the rate of temperature change in the heat sink. In operation 116, the method 100 includes determining the rate of temperature change in the metal object using a thermographic camera. In operation 120, the method 100 includes determining a difference between the heat transfer profile and a baseline profile. If the difference between the baseline profile and the heat transfer profile is within an error threshold, then in decision block 124, the method progresses to operation 100. In operation 128, the method includes indicating that the composition of material in the metal object is verified.

If the difference between the baseline profile and the heat transfer profile is outside or exceeds the error threshold, then in decision block 124, the method 100 progresses to operation 132. In operation 132, the method includes indicating that the composition of material in the metal object is not verified.

Figure 11A:
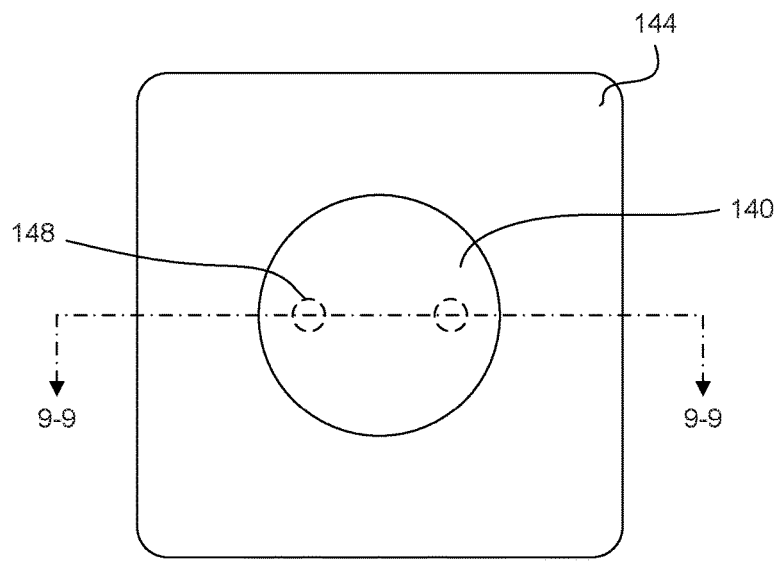
FIG. 11A depicts a top view of a coin in a display case, according to one or more embodiments.

Referring to FIG. 11A a top view of a coin 140 in a display case 144 is depicted, according to one or more embodiments. In various instances, coins, bullion bars and bricks are sealed in a hard plastic protective case to protect the metal object to maintain the quality, value, and luster of the coin or bar. Depicted in FIG. 11A, in one or more embodiments, a display case 140 may include one or more testing contacts 148 included therein. Each of the testing contacts 148 may be in thermal contact with the coin 144 or other protected object, and made of silver, copper, or other thermally conductive material.

Figure 11B:
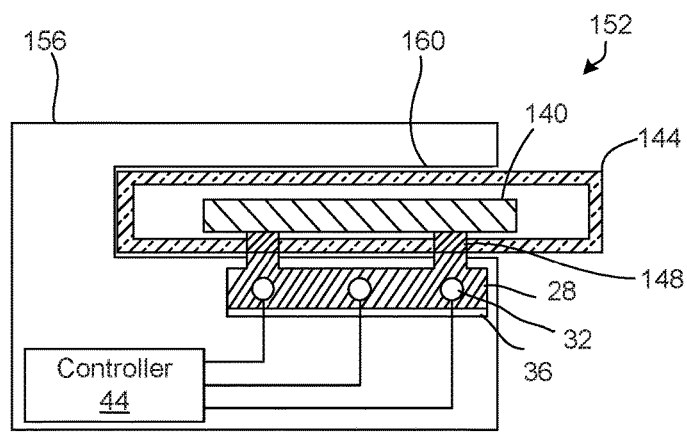
FIG. 11B depicts a cross-section view of the coin and display case taken at line 9-9 of FIG. 9A in a testing apparatus, according to one or more embodiments.

Referring to FIG. 11B, a testing apparatus 152 for the display case and coin is depicted, according to one or more embodiments. Testing apparatus 152 may share the same or similar components as the testing apparatus 20 in FIGS. 1-3, which are indicated using shared reference numerals. For example, testing apparatus 152 may include a heat sink 28, a group of temperature sensors 32, a heating element 36, and a controller 44.

In addition, testing apparatus 152 includes a housing 156 including a slot 160 for insertion of the display case 144 and coin 140. Once inserted, testing contacts 148 align with the heat sink 28 and form a thermal connection from the heat sink to the coin 144. Per FIGS. 11A and 11B, there are two testing contacts 148. However in some embodiments, there may be fewer or more testing contacts 148 depending on the design of the display case 144 and the coin 140.

In operation, the controller 44 and heating element 36 establish a temperature differential between the coin 144 and the heat sink 28. The display case 144 is inserted into the housing 156 and the controller may initiate the testing sequence, as described above.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to explain the principles of the embodiments, the practical application or technical improvement over technologies found in the marketplace, or to enable others of ordinary skill in the art to understand the embodiments disclosed herein.

What is claimed is:

1. A system for verifying a purported composition of material in a solid metal object based on heat transfer characteristics, the system comprising:
   a heat sink including a group of temperature sensors embedded therein;
   a controller communicatively connected to the group of temperature sensors, the controller including:
   a processor; and
   a memory, the memory including a set of instructions executable on the processor to:
   determine, using the group of temperature sensors, a heat transfer profile for the heat sink when connected to the solid metal object, the heat transfer profile indicating temperature of the heat sink with the solid metal object over a testing interval, the heat sink having a temperature differential with the solid metal object at least at a beginning of the testing interval;
   compare the heat transfer profile for the solid metal object to a baseline heat transfer profile determined based on dimensions of the solid metal object and the purported composition;
   determine, based on the comparing, a difference between the heat transfer profile and the baseline heat transfer profile; and
   indicate, using the controller, that the purported composition is verified, in response to determining that the difference between the heat transfer profile and the baseline heat transfer profile is within a threshold.

2. The system of claim 1, wherein the set of instructions are further executable on the processor to:
   determine, using the group of temperature sensors, a second heat transfer profile for the heat sink when connected to a second solid metal object having the purported composition of material and the dimensions of the solid metal object, the second heat transfer profile indicating temperature of the heat sink with the second solid metal object over a second testing interval, the heat sink having the temperature differential with the second solid metal object at least at a beginning of the second testing interval;
   compare the second heat transfer profile to the baseline heat transfer profile;
   determine, based on the comparing, a difference between the second heat transfer profile and the baseline heat transfer profile; and
   indicate that the purported composition is not verified in response to determining that the difference between the second heat transfer profile and the baseline profile is outside of the threshold.

3. The system of claim 1, wherein the set of instructions are further executable on the processor to:
   establish the temperature differential between the heat sink and the solid metal object.

4. The system of claim 1, wherein;
   the heat sink is a hemispherical portion of silver having a body portion and a flat portion for supporting the solid metal object; and
   the heat sink is included in a testing platform including a substantially planar portion of insulating material enclosing the body portion.

5. The system of claim 1, further comprising:
   a thermographic camera configured to observe temperature gradients of the heat sink with the solid metal object.

6. The system of claim 5, wherein:
   the instructions being executable to determine the heat transfer profile includes being executable to collect thermographic images of the heat sink with the solid metal object over the testing interval; and wherein the heat transfer profile further indicates temperature gradients of the of the heat sink with the solid metal object over the testing interval.

\* \* \* \* \*